(12) United States Patent
Lawandy

(10) Patent No.: US 10,139,342 B2
(45) Date of Patent: Nov. 27, 2018

(54) PHOTOLUMINESCENT AUTHENTICATION DEVICES, SYSTEMS, AND METHODS

(71) Applicant: Spectra Systems Corporation, Providence, RI (US)

(72) Inventor: Nabil Lawandy, Saunderstown, RI (US)

(73) Assignee: Spectra Systems Corporation, Providence, RI (US)

( * ) Notice: Subject to any disclaimer, the term of this patent is extended or adjusted under 35 U.S.C. 154(b) by 0 days.

(21) Appl. No.: 15/402,968

(22) Filed: Jan. 10, 2017

(65) Prior Publication Data

US 2017/0191934 A1 Jul. 6, 2017

Related U.S. Application Data

(63) Continuation-in-part of application No. 14/817,427, filed on Aug. 4, 2015.

(60) Provisional application No. 62/342,577, filed on May 27, 2016, provisional application No. 62/406,271, filed on Oct. 10, 2016.

(51) Int. Cl.
*G01N 21/64* (2006.01)
*G07D 7/12* (2016.01)
*G07D 7/1205* (2016.01)

(52) U.S. Cl.
CPC ....... *G01N 21/6408* (2013.01); *G07D 7/1205* (2017.05)

(58) Field of Classification Search
CPC .......... G07D 7/122; G07D 7/12; G01N 21/64; G01N 21/6408; G01N 21/78; G01N 21/6428

USPC .......... 250/459.1, 458.1, 556, 271
See application file for complete search history.

(56) References Cited

U.S. PATENT DOCUMENTS

| | | | |
|---|---|---|---|
| 4,591,707 A * | 5/1986 | Stenzel | B41M 3/14 235/448 |
| 2004/0061048 A1* | 4/2004 | Vasic | G01N 21/6408 250/271 |
| 2004/0233465 A1* | 11/2004 | Coyle | B41M 3/008 358/1.9 |
| 2005/0178841 A1* | 8/2005 | Jones, II | C09D 11/50 235/468 |
| 2006/0159329 A1* | 7/2006 | Joshi | G07D 7/1205 382/135 |
| 2007/0295116 A1* | 12/2007 | Le Mercier | C09K 11/7777 73/866 |
| 2010/0084541 A1* | 4/2010 | Peregrym | G03F 7/70291 250/202 |
| 2011/0199222 A1 | 8/2011 | Lawandy | |
| 2012/0132830 A1 | 5/2012 | Monro et al. | |

(Continued)

OTHER PUBLICATIONS

Written Opinion of the International Searching Authority in PCT/US16/44863 (dated Oct. 18, 2016).

*Primary Examiner* — David Porta
*Assistant Examiner* — Blake Riddick
(74) *Attorney, Agent, or Firm* — Pryor Cashman LLP

(57) ABSTRACT

A system and method for authenticating an item such as a banknote, including a photoluminescent material absorbing an incident radiation from a radiation source and emitting an emitted radiation having a spectral signature with a decay time after removal of the radiation source, and a sensor detecting the spectral signature in the emitted radiation during the decay time.

17 Claims, 11 Drawing Sheets

(56) References Cited

U.S. PATENT DOCUMENTS

| | | | |
|---|---|---|---|
| 2013/0020504 A1* | 1/2013 | Kraemer | G01N 21/6408 |
| | | | 250/459.1 |
| 2013/0153789 A1* | 6/2013 | Smith | G01N 21/63 |
| | | | 250/459.1 |
| 2013/0165180 A1* | 6/2013 | Fukuda Kelley | G05B 19/02 |
| | | | 455/556.1 |
| 2013/0308045 A1* | 11/2013 | Rhoads | H04N 5/2256 |
| | | | 348/371 |
| 2014/0061486 A1 | 3/2014 | Bao et al. | |
| 2014/0210998 A1* | 7/2014 | Pawlik | G07D 7/12 |
| | | | 348/135 |
| 2014/0211071 A1* | 7/2014 | Pawlik | G07D 7/12 |
| | | | 348/335 |
| 2014/0233842 A1* | 8/2014 | Gardner | G07D 7/00 |
| | | | 382/143 |
| 2014/0362228 A1* | 12/2014 | McCloskey | H04N 5/33 |
| | | | 348/164 |
| 2015/0036138 A1* | 2/2015 | Watson | G01N 21/31 |
| | | | 356/402 |
| 2016/0140427 A1* | 5/2016 | Keay | G07D 7/121 |
| | | | 235/494 |
| 2017/0301169 A1* | 10/2017 | Ghauch | G07D 7/1205 |

* cited by examiner

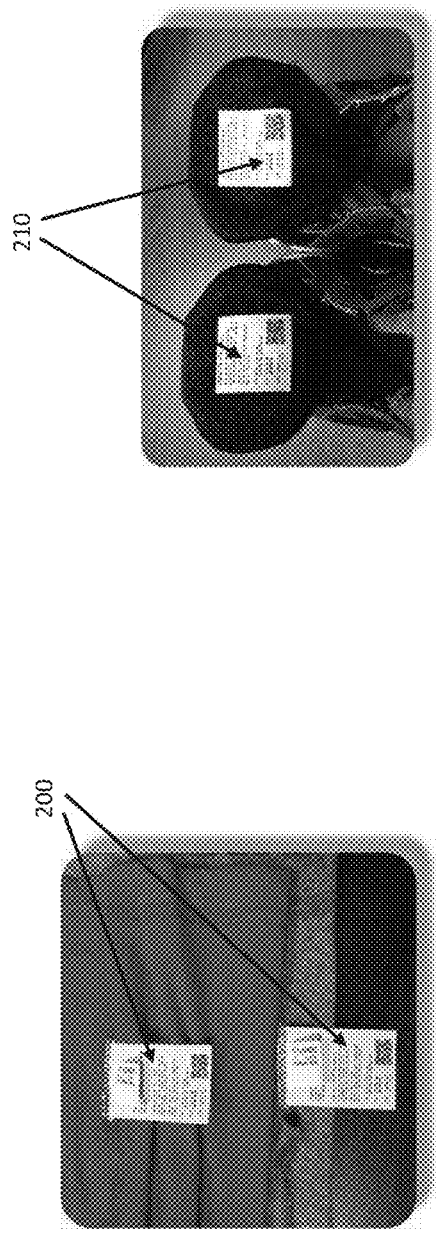
FIGURE 2A
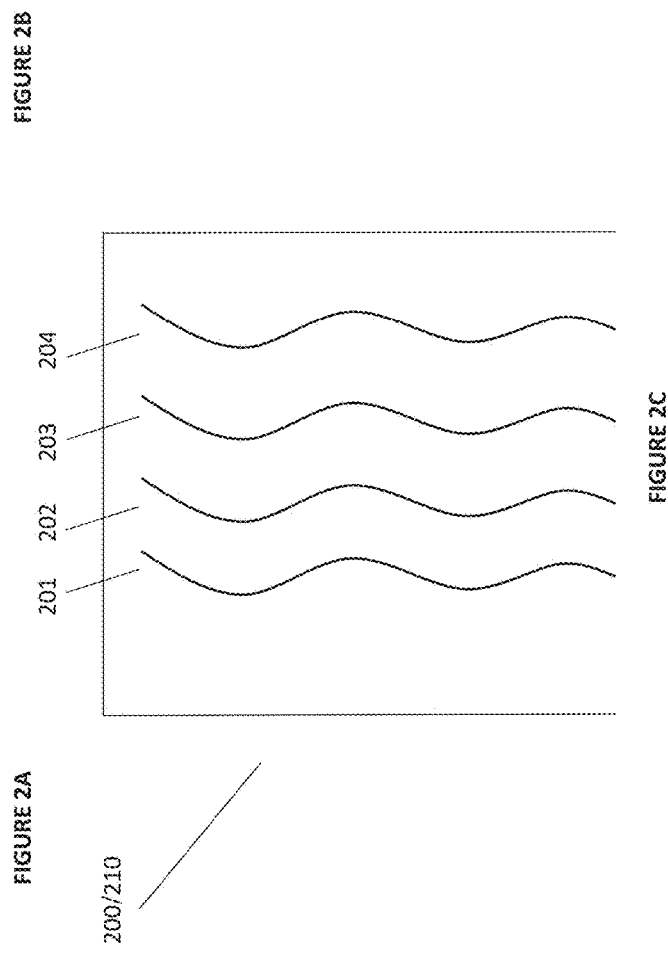
FIGURE 2B
FIGURE 2C

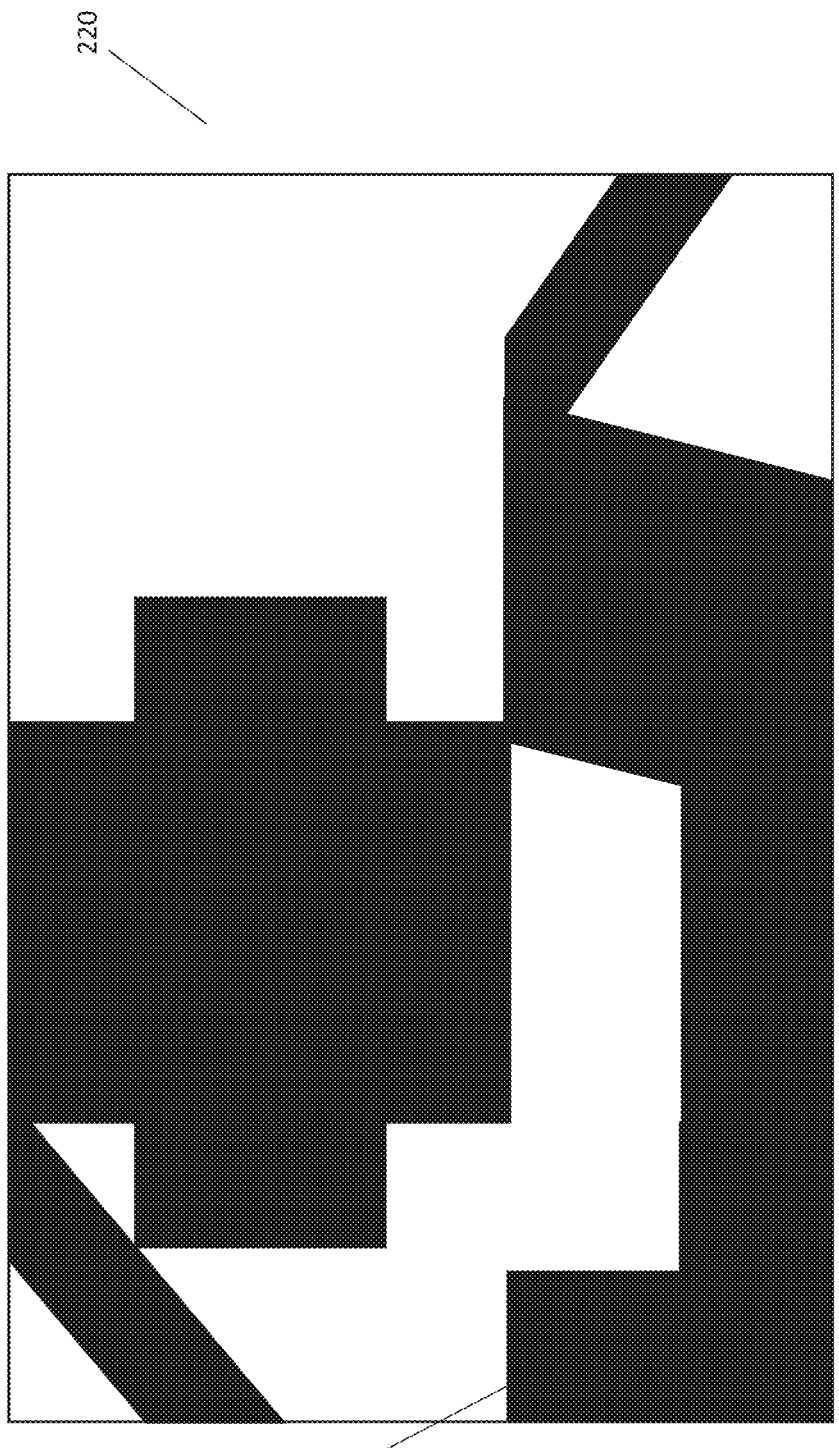

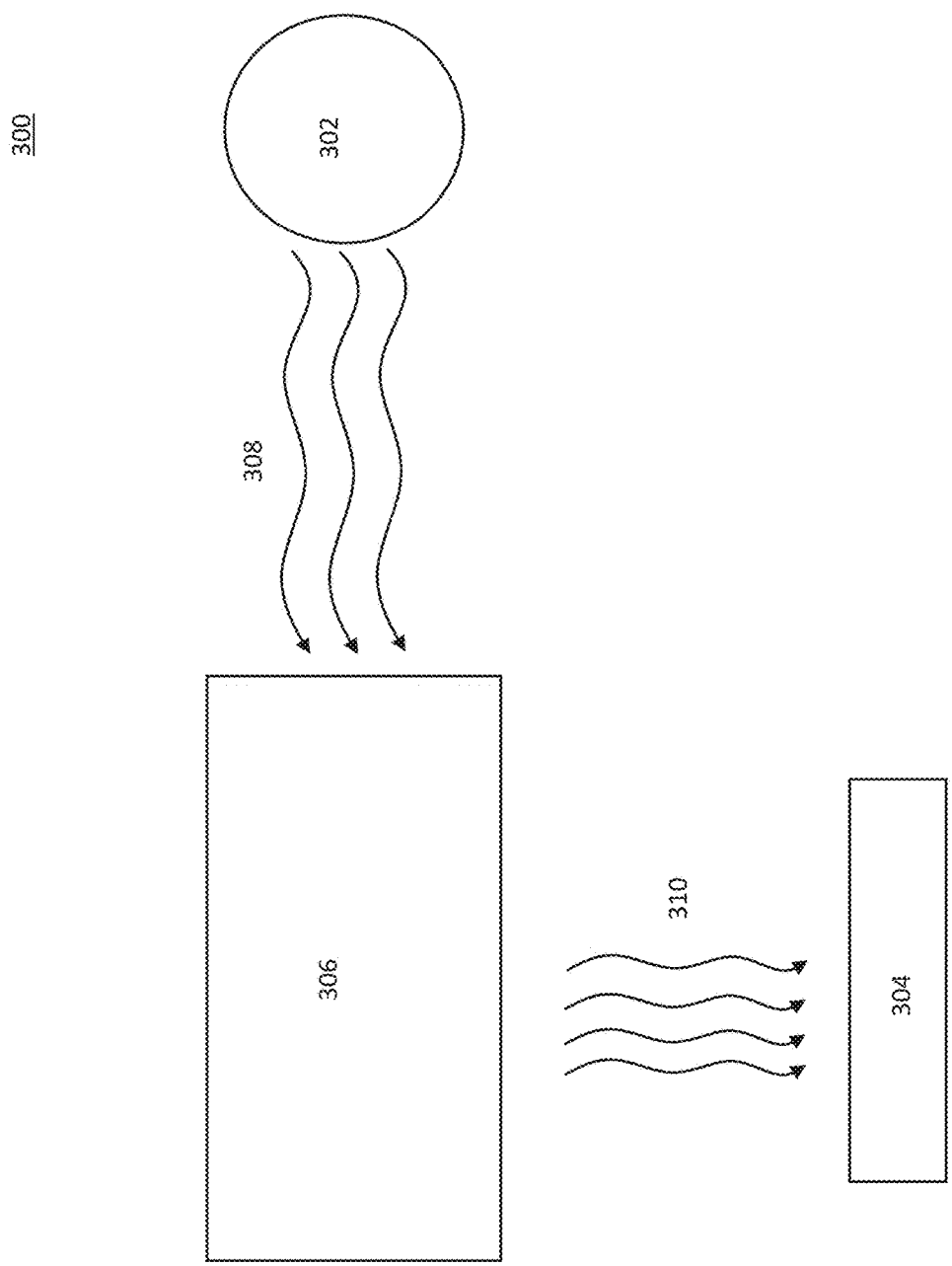

PHOTOLUMINESCENT AUTHENTICATION DEVICES, SYSTEMS, AND METHODS

CROSS-REFERENCE TO RELATED APPLICATIONS

The application is a continuation-in-part of U.S. patent application Ser. No. 14/817,427, filed Aug. 4, 2015. This application claims priority to U.S. provisional application Ser. No. 62/342,577, filed May 27, 2016 and U.S. provisional application Ser. No. 62/406,271, filed Oct. 10, 2016.

FIELD

The present application generally relates to devices, apparatus, systems and methods for authenticating items. Specifically, the present application relates to using a photoluminescent label or photoluminescent materials for authenticating items.

BACKGROUND

Counterfeiting is a growing business and economic concern. Various products and items are subject to counterfeiting. For example, tax stamps for products such as liquor and tobacco, apparel, footwear, ink cartridges, currency, automotive parts, and electronics can all be subject to counterfeiting. Counterfeit products are often difficult to detect and are typically of inferior quality. Counterfeit products have an adverse impact on both consumers and manufacturers, and could even be harmful and/or dangerous to unsuspecting consumers.

Manufacturers attempt to discourage and prevent counterfeiting through various techniques. For example, some manufacturers of products targeted by counterfeiters have utilized specific markings, holograms, stamps, or other features on their products. Nevertheless, these techniques can typically be circumvented by counterfeiters. Another anti-counterfeiting technique that has been the use of radio frequency identification (RFID) tags; however, RFID tags can be expensive, and the technology needed to identify the data transmitted by each RFID tag is not readily available to consumers.

Accordingly, there is a need for cost-effective and accurate authentication of products that is accessible and easy to use by consumers, while being difficult for counterfeiters to circumvent.

BRIEF SUMMARY

In general, in one aspect, the invention features a system for authenticating an item, the system including a photoluminescent material absorbing an incident radiation from a radiation source and emitting an emitted radiation having a spectral signature with a decay time after removal of the radiation source, and a sensor detecting the spectral signature in the emitted radiation during the decay time.

Implementations of the invention may include one or more of the following features. The detected spectral signature may include a detected spectral intensity at a first wavelength and a detected spectral intensity at a second wavelength to define a measured code. The detected code may be compared to a predetermined code to determine authentication. The spectral signature may include a spectral pattern or a spatial pattern. The detected spectral signature may include a detected spectral intensity at a third wavelength. The sensor may include at least one of a smartphone and a tablet, and may include an imaging device. At least one of the first and second wavelengths in the emitted radiation may within a spectrum of visible light on non-visible light. The decay time may be at least one second.

The photoluminescent material may be included in a label on the item, which may be tamper-proof. The photoluminescent material may be incorporated into a currency. The photoluminescent material may be included in a coating applied directly or indirectly onto the item, which may resist wear of the item.

The sensor may communicate with an application to verify the authenticity of the item. The application may be operated by a touch screen or audibly by voice. The application may report the results of verifying the authenticity of the item to an authority, and the application may report the location of the item to the authority.

In general, in another aspect, the invention features a method for authenticating an item, including irradiating, with a radiation source, a photoluminescent material absorbing an incident radiation and emitting an emitted radiation having a spectral signature with a decay time, removing the radiation source, detecting the spectral signature in the emitted radiation during the decay time, generating a code based on the spectral signature, and comparing the code to a predetermined reference code.

Implementations of the invention may include one or more of the following features. The spectral signature may include a spectral intensity at a first wavelength, a spectral intensity at a second wavelength, and a spectral intensity at a third wavelength. The detecting may include scanning the emitting radiation.

The item may be a banknote, and the method may further include verifying the authenticity of the banknote and determining a denomination of the banknote.

In general, in another aspect, exemplary embodiments of the present invention may provide a system for authentication, including a photoluminescent material having a decay time, the photoluminescent material configured to absorb an incident radiation from a radiation source and to emit an emitted radiation having a spectral signature after removal of the radiation source, and a sensor configured to measure the spectral signature in the emitted radiation during the decay time.

Implementations of various exemplary embodiments of the present invention may include one or more of the following features. The measured spectral signature may include a measured spectral intensity at a first wavelength and a measured spectral intensity at a second wavelength to define a measured code. According to certain aspects, the measured spectral signature may include a measured spectral intensity at a third wavelength. These wavelengths may be in the spectrum of visible light or non-visible light. The sensor may be configured to perform the measurement during the decay time of the photoluminescent material. This decay time may be at least one second, and the spectral signature may include a spectral and spatial pattern. The measured code may be compared to a predetermined code to determine authentication. The sensor may be a smartphone or a tablet, and the sensor may be an imaging device. The photoluminescent label may be configured to be incorporated into a currency. The photoluminescent material may be included in a coating applied directly or indirectly onto an item. Further, the sensor is connected to an application on the smartphone or tablet and the application verifies the authenticity of the item.

In general, in another aspect, exemplary embodiments of the invention may provide a method for authenticating an item including irradiating, with a radiation source, a photoluminescent material having a decay time and being configured to absorb an incident radiation and to emit an emitted radiation having a spectral signature after removal of the radiation source, measuring, with a sensor, the spectral signature in the emitted radiation during the decay time, generating, with a computing device, a code based on the spectral signature, and comparing, with the computing device, the code to a predetermined reference code.

Implementations of various exemplary embodiments of the present invention may include one or more of the following features. The label may be further configured such that the spectral signature includes a spectral intensity at a first wavelength, a spectral intensity at a second wavelength, and a spectral intensity at a third wavelength. The sensor may be a smartphone or a tablet. The sensor may be connected to an application on the smartphone or tablet. Further, the photoluminescent material may be included in a coating applied directly or indirectly onto an item.

BRIEF DESCRIPTION OF THE DRAWINGS

FIG. 2A is an illustration of an exemplary photoluminescent label according to certain exemplary embodiments of the present invention;

FIG. 2B is an illustration of an exemplary photoluminescent label according to certain exemplary embodiments of the present invention;

FIG. 2C is a diagram of an exemplary photoluminescent label according to certain exemplary embodiments of the present invention;

FIG. 2D is an illustration of an exemplary spatial pattern of an exemplary photoluminescent label according to certain exemplary embodiments of the present invention;

FIG. 3 is a diagram of an exemplary photoluminescent authentication system according to certain exemplary embodiments of the present invention;

DETAILED DESCRIPTION

Figure 1B:
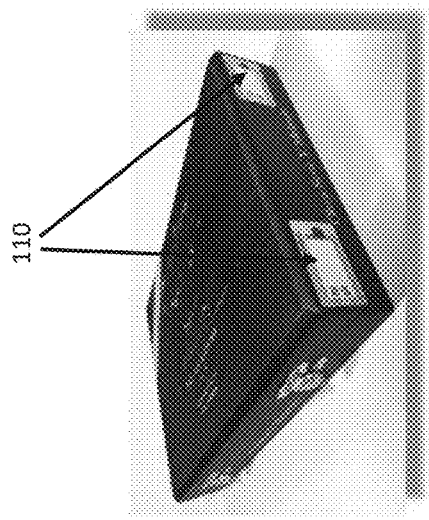
FIG. 1B is an illustration of an exemplary photoluminescent label according to certain exemplary embodiments of the present invention.

Exemplary embodiments of the present invention are generally directed to devices, apparatus, systems, and methods for authentication using photoluminescence. Specifically, exemplary embodiments of the present invention provide a label including a photoluminescent material and associated detecting/sensing mechanisms that may be used to authenticate an item to which the label is affixed. Although the exemplary embodiments of the present invention are primarily described with respect to authentication and/or preventing counterfeiting, it is not limited thereto, and it should be noted that the exemplary photoluminescent label may be used to encode other types of information for other applications. Further, the exemplary embodiments of the present invention may be used in conjunction with other authentication measures, e.g., holograms, watermarks, and magnetic encoding.

An exemplary embodiment of the present invention provides a label including a photoluminescent material and a sensor or scanner to image and/or read a code encoded on the label. According to an exemplary embodiment of the present invention, the photoluminescent label includes a photoluminescent material. The photoluminescent material may be configured to absorb an incident radiation, and emit an emitted radiation having a spectral signature after removal of the source of the incident radiation. According to certain exemplary embodiments of the present invention, the spectral signature may include spectral intensities at certain wavelengths, and the photoluminescent material may be selected and configured such that the emitted radiation has known intensities at specific wavelengths. For example, the photoluminescent material may be excited by irradiating the photoluminescent material with an incident radiation such as, e.g., visible light, which is absorbed by the photoluminescent material, and the photoluminescent material may then emit radiation having a spectral signature, such as, each of red ("R"), green ("G"), and blue ("B") light at known spectral intensities. Alternatively, the photoluminescent material may be applied in a specific spatial pattern, and the spectral signature may include spectral intensities emitted by the patterned photoluminescent material. The spectral signature, which may include, e.g., spectral intensities at the particular wavelengths or a patterned spectral signature, can effectively be used as a code. This code, for example, may be used to authenticate the item to which the label is attached. This code can be created with any number of selected spectral intensities and, thus, more complex and intricate codes can be created by using a greater number of selected spectral intensities at particular wavelengths. Thus, the photoluminescent material may be specifically selected for the incident radiation and the desired spectral intensities in the emitted radiation. According to exemplary embodiments of the present invention, the desired spectral intensities may include the particular wavelengths and the relative and absolute amplitudes of the spectral intensities at the particular wavelengths.

Preferably, the photoluminescent material has a long decay time during which emitted radiation is emitted, e.g., greater than 1 second, such as is the case for a phosphorescent material. According to certain exemplary embodiments of the present invention, the photoluminescent material may have a decay time of any length, such as a tenth of a second, a quarter of a second, half a second, one second, or multiple seconds, e.g., 2, 3, 4, 5, or more seconds. The long decay time would enable a user sufficient time to scan or image the photoluminescent label during the decay time so that the user can obtain a measurement of the spectral intensities at particular wavelengths of the emitted radiation. Further, the photoluminescent material may be applied to virtually any surface or material, thus allowing the use of the exemplary photoluminescent label for a wide range of applications. Accordingly, the exemplary photoluminescent label is not limited to flat and/or smooth surfaces and can be used on flexible materials such as fabrics, paper, and other substrates, and may be incorporated onto the item itself. According to certain exemplary embodiments, the coating can be disposed under the surface of the label and may be excited and scanned and/or imaged through the surface of the label.

Figure 1A:
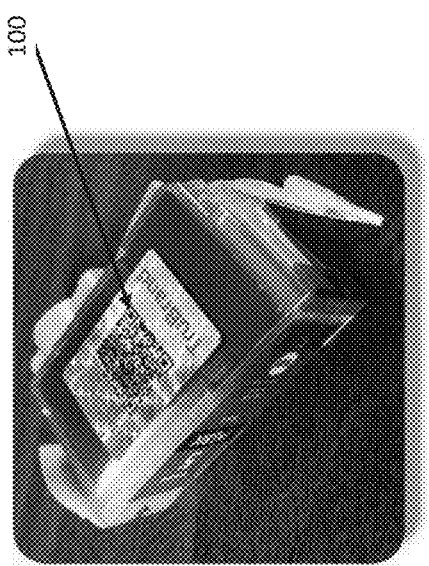
FIG. 1A is an illustration of an exemplary photoluminescent label according to certain exemplary embodiments of the present invention.
Figure 1C:
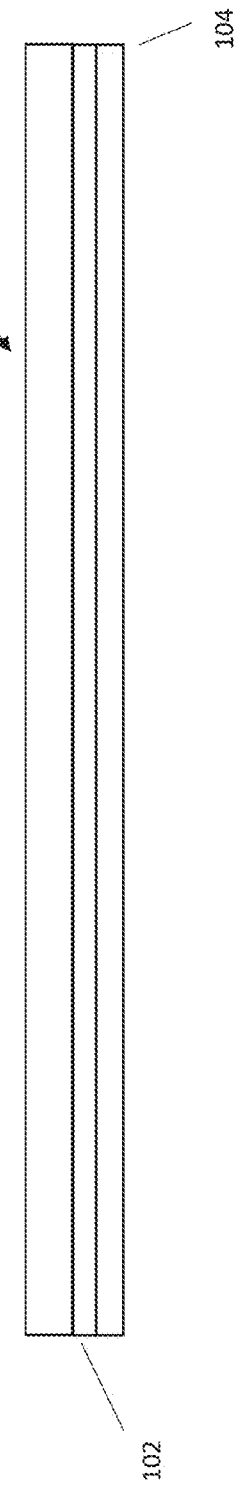
FIG. 1C is a diagram of an exemplary photoluminescent label according to certain exemplary embodiments of the present invention.

In accordance with exemplary embodiments of the present invention, FIGS. 1A and 1B show exemplary photoluminescent labels 100 and 110 attached to consumer products. Although label 100 is a holographic label attached to a printer ink cartridge, label 100 can be attached to any product or product packaging and can be part of other types of labels, such as, e.g., barcode labels and QR-codes. FIG. 1B shows photoluminescent label 110 as a tax stamp affixed to a tobacco product. As with photoluminescent label 100, photoluminescent label 110 can be incorporated onto other labels, such as stamps, on virtually any product. FIG. 1C shows a magnified, generalized cross-sectional view of photoluminescent labels 100 and 110. As shown in FIG. 1C, the photoluminescent material 102 may be applied to the back of the label 100.

According to certain exemplary embodiments of the present invention, photoluminescent material 102 may include storage phosphors and long decay phosphors containing rare earth metals and transition metals, and various hosts including glasses such as phosphates and aluminosilicates. Further, this photoluminescent material may be added as a coating to any label during the manufacturing process of the label, and in particular, may be included in a binder material attached to the bottom of the label. Preferably, an adhesive, or other affixing element 104 may be applied over the photoluminescent material so that the label can be affixed to a product or a package. Alternatively, photoluminescent material 102 may be applied to the front or top of the label, and a protective coating may be applied over the photoluminescent material 102. According to yet another embodiment of the present invention, photoluminescent material 102 may be directly applied to an item, such as currency, which may require the item itself, rather than the packaging, to be authenticated.

FIGS. 2A and 2B show further exemplary photoluminescent labels 200 and 210 according to certain exemplary embodiments of the present invention. As shown in FIGS. 2A and 2B, photoluminescent labels 200 and 210 are fabric labels that may be attached to certain apparel, such as the photoluminescent label 200 as shown in FIG. 2A, or footwear, such as the photoluminescent label 210 as shown in FIG. 2B.

Similar to photoluminescent labels 100 and 110, photoluminescent labels 200 and 210 may include a photoluminescent material which may be applied as a coating having a printed or spatial pattern onto the fabrics that make up photoluminescent labels 200 and 210. Alternatively, as shown in FIG. 2C, photoluminescent labels 200 and 210 may be constructed from individual threads bearing photoluminescent material. For example, according to an exemplary embodiment of the present invention, at least one of threads 201, 202, 203, and 204 may contain a photoluminescent material, and threads 201-204 can be woven together to create photoluminescent labels 200 and 210. According to certain exemplary embodiments, threads 201, 202, 203, and 204 may all contain the same photoluminescent material. Alternatively, each of threads 201, 202, 203, and 204 may contain a different photoluminescent material, each of which may have differing absorption and emission characteristics. Further, the denier of the threads, e.g., 20-80, may be varied to vary the amount of photoluminescent material that is contained on each thread. Accordingly, the denier of the threads and the types of photoluminescent material applied to each of the threads may be specifically selected and/or patterned to obtain a spectral and spatial signature, such as specific emission characteristics to yield certain spectral intensities or a spectral and spatial pattern, to create unique codes. For example, threads 201 and 203 may have a certain denier and contain a first type of photoluminescent material, and threads 202 and 204 may have a different denier and contain a second type of photoluminescent material. Alternatively, threads 201-204 may each contain a different type of photoluminescent material. In some embodiments, some of threads 201-204 may not contain any photoluminescent material. Accordingly, any combination or permutation of different deniers and photoluminescent materials may be utilized and patterned to specifically obtain a spectral and spatial signature, such as desired emission characteristics and spectral intensities or a desired spectral and spatial pattern, in the radiation emitted by the photoluminescent labels 200 and 210 in creating unique codes. FIG. 2D shows an exemplary label 220, with the shaded portions representing an exemplary spectral and spatial pattern 222 which may be emitted by photoluminescent labels 200 and 210.

Figure 8:
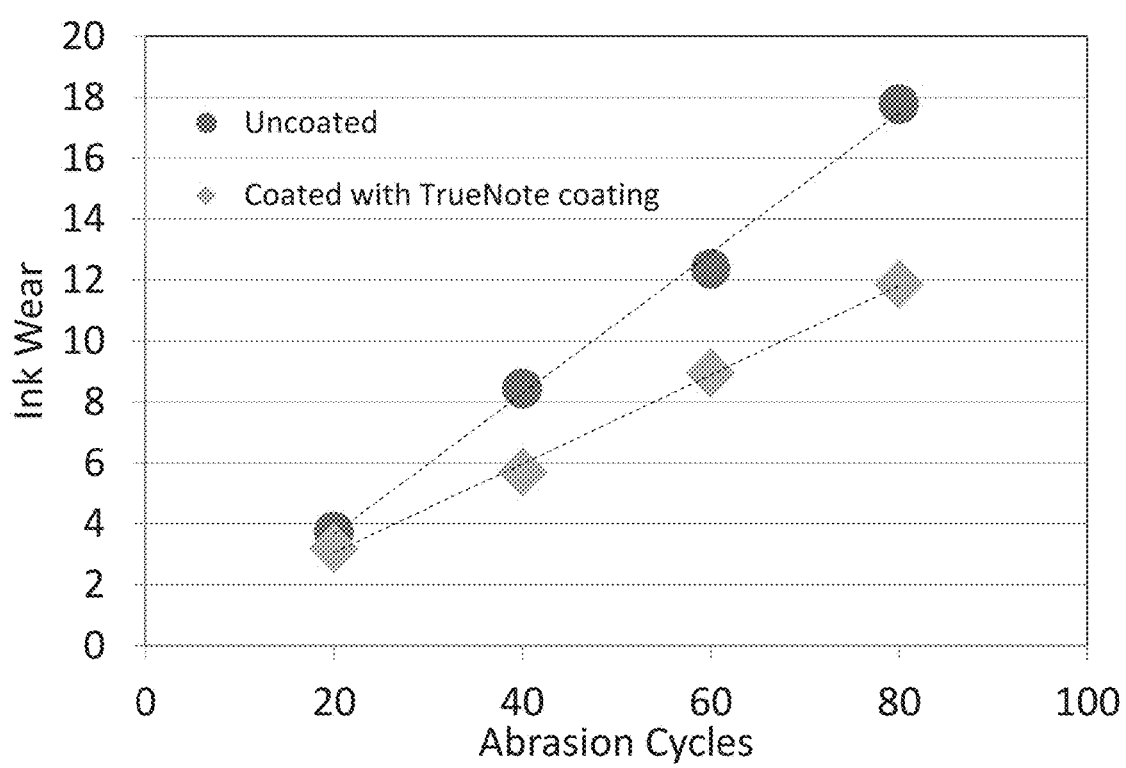
FIG. 8 illustrates the application of a photoluminescent material as an overcoat on a banknote to increase ink wear resistance.

In an alternative embodiment, a photoluminescent material that functions in accordance with the present invention may be included in a coating applied directly or indirectly onto a substrate such as a fabric. Such a coating may have additional beneficial properties, such as to protect the substrate or features of the substrate. For example, as shown in FIG. 8, the photoluminescent material operating in accordance with the present invention may be applied as a transparent coating or overcoat on a banknote, such as a polymer banknote. Such an overcoat including nano-materials may provide the additional benefit of ink wear resistance, e.g., to increase the life of polymer banknotes. An overcoat for banknotes as described herein may have up to 50% greater ink wear resistance compared to uncoated banknotes, and the process for its application to the substrate may be compatible with lithographic and flexographic printing.

As shown in FIG. 8, the ink wear on a polymer banknote increases more slowly as the number of abrasion cycles applied to the banknotes increases if the banknote is covered with an ink wear resistance coating. The graph shown in FIG. 8 shows an accelerated wear test of ink on a polymer Mexican 50-peso note. Rub-wear action was produced using a Taber Abrasion Tester (Model 5130) by contact of the test banknote against the sliding rotation of two abrading wheels. After each 20 abrasion cycles on the Tester, the banknote's diffuse reflectance was measured using a Data-Color 650 spectrophotometer after each set of wear cycles to measure the removal of banknote ink from the banknote.

FIG. 3 shows an exemplary system 300 in accordance with exemplary embodiments of the present invention. As shown in FIG. 3, system 300 may include a radiation/ excitation source 302, a sensor 304, and a photoluminescent label 306. Radiation/excitation source 302 may be any source supplying radiation 308, such as, e.g., visible light, ultraviolet, radio, or microwave, which is to be absorbed by photoluminescent label 306. The photoluminescent label 306 may re-emit emitted radiation 310 at the same wavelengths or emit emitted radiation 310 at different wavelengths. Sensor 304 may include any detecting, sensing, imaging, or scanning device that is able to receive, image, and/or measure the spectrum of the radiation emitted by the photoluminescent label 304, such as a photometer or digital camera. According to certain exemplary embodiments of the present invention, radiation/excitation source 302 may include the flash of a digital camera, and sensor 304 may include the optical components and sensors of the digital camera. In one exemplary embodiment, the radiation/excitation source 302 may include the light source of a smartphone or tablet camera, e.g., Apple iPhone, Apple iPad, Samsung Galaxy or other Android devices, and sensor 304 may include the camera of the smartphone or tablet. For example, the light source and the lens of a smartphone or tablet camera can be moved across a surface of the photoluminescent label 306 to sequentially excite photoluminescent label 306 by irradiating photoluminescent label 306 with the light source of the smartphone or tablet and, after the excitation has been removed, measure the spectrum of the emitted radiation with the smartphone or tablet camera in a single motion. Further, photoluminescent label 306 may include any of photoluminescent labels 100, 110, 200, or 210 described herein, and may be attached or affixed to any product or item, e.g., tax stamps, apparel, currency, or footwear, for which authentication may be desirable.

Figure 4A:
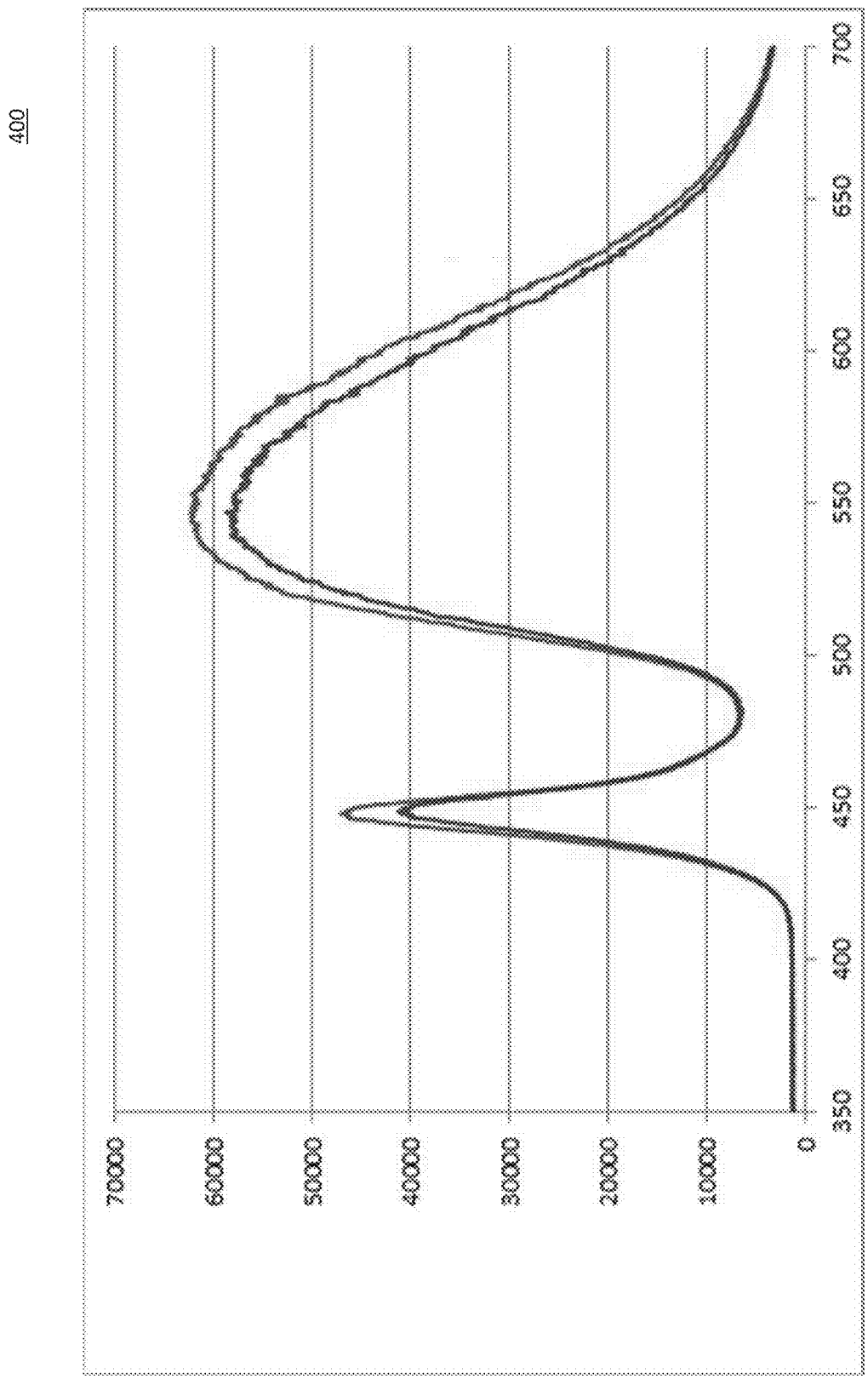
FIG. 4A is a graph showing certain representative spectral characteristics of an exemplary radiation source according to certain exemplary embodiments of the present invention.
Figure 4B:
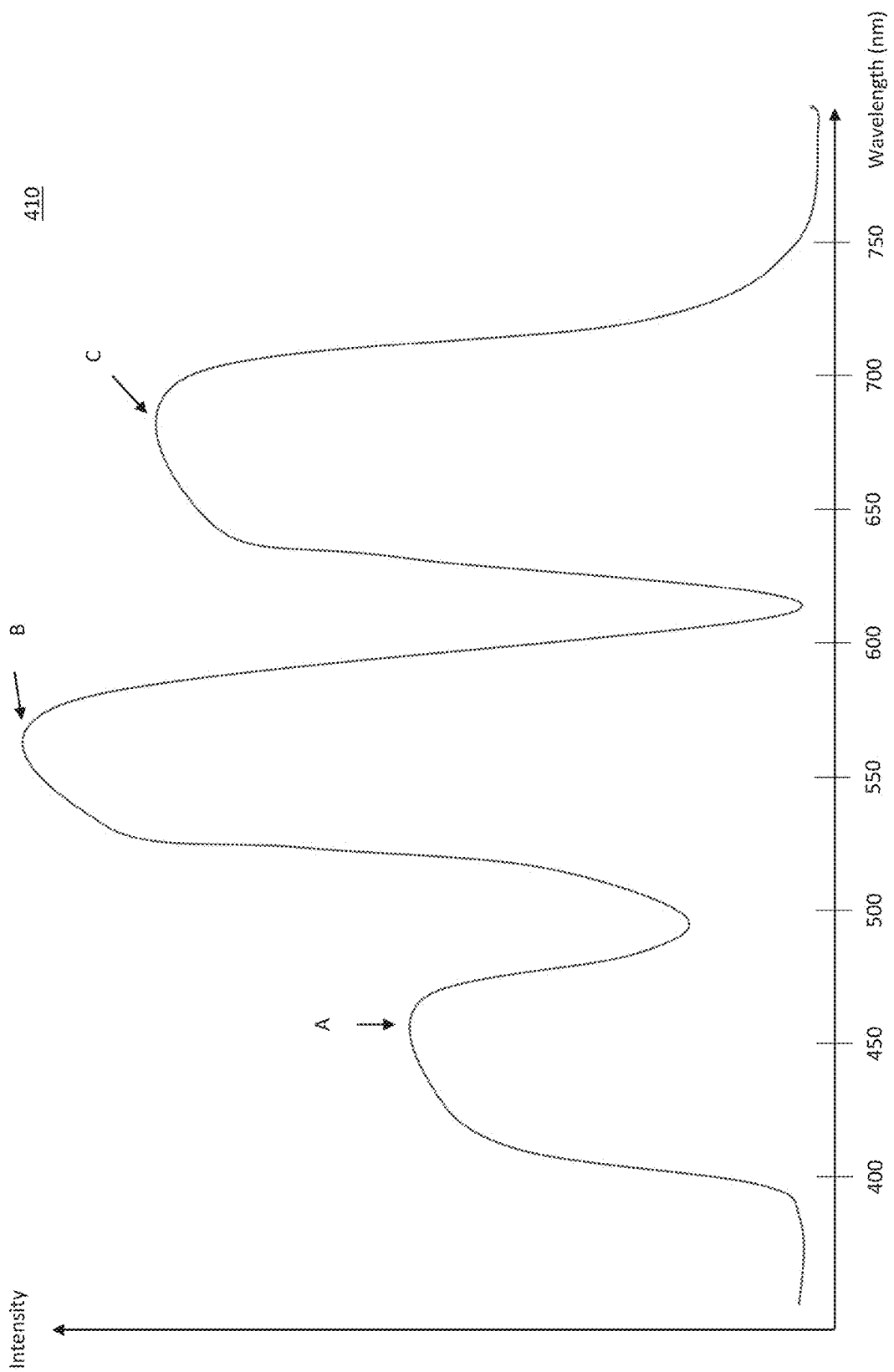
FIG. 4B is a graph showing certain representative spectral characteristics of exemplary emitted radiation according to certain exemplary embodiments of the present invention.
Figure 4C:
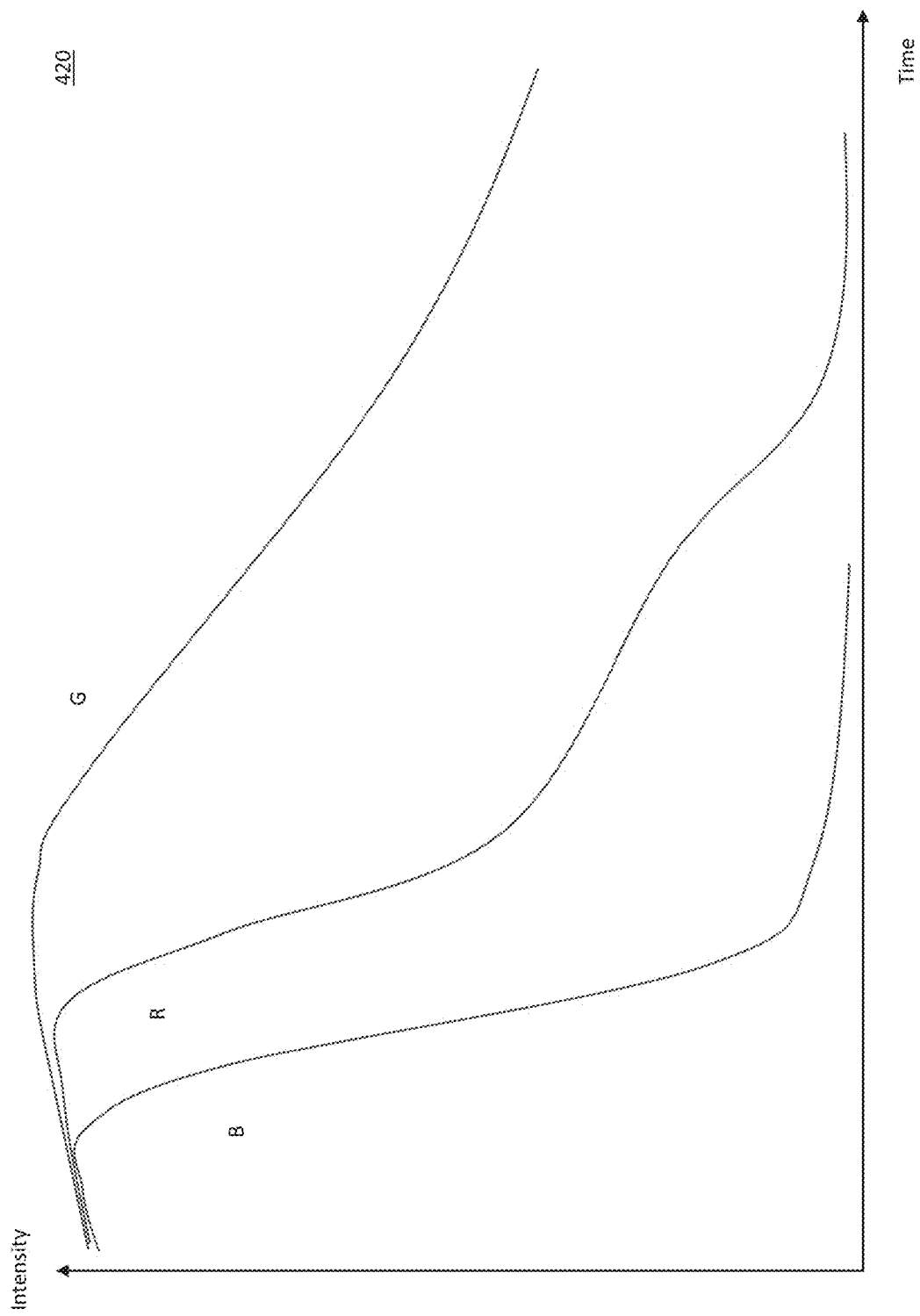
FIG. 4C is a graph showing certain representative spectral characteristics of exemplary emitted radiation according to certain exemplary embodiments of the present invention.

FIGS. 4A, 4B, and 4C are exemplary graphs representing certain representative characteristics of the incident and emitted radiations according to exemplary embodiments of the present invention. The depictions in graphs 400, 410, and 420 are merely representative, and exemplary embodiments of the present invention may employ any variation of decay times, as well as spectral intensity characteristics, such as the number of spectral intensities used, the wavelengths at which the spectral intensities are measured, and the amplitude of the spectral intensities. FIG. 4A shows an exemplary graph 400 of representative spectral intensities of an exemplary incident radiation/excitation source. For example, graph 400 shows the spectral intensities of a smartphone camera light source used in two different modes. As shown in graph 400, the exemplary incident radiation includes higher spectral intensities near the 450 nm and the 550 nm wavelengths, which generally correspond to blue and green light, respectively. It should be noted that the spectral intensities of various light sources may vary widely, and the spectral intensities of the incident radiation absorbed by the photoluminescent label may affect the spectral characteristics of the radiation emitted by the photoluminescent label.

FIG. 4B shows an exemplary graph 410 of representative spectral intensities of emitted radiation that may be used to compose an exemplary code in accordance with exemplary embodiments of the present invention, and FIG. 4C shows an exemplary graph 420 of representative relative decay times of certain wavelengths of the emitted radiation. As shown in FIG. 4B, exemplary graph 410 depicts representative relative spectral intensities of an exemplary spectrum of radiation. According to certain exemplary embodiments of the present invention, the spectral intensities at points A, B, and C, or any other point in the spectrum, may be used to create a unique code encoded on a photoluminescent label. According to certain exemplary embodiments of the present invention, wavelengths in the visible light spectrum or the non-visible light spectrum may be used.

FIG. 4C shows an exemplary graph 420 of representative relative decay times of certain wavelengths of the emitted radiation. As shown in graph 420, each of the wavelengths of radiation in the emitted radiation may decay at a different rate. In view of the variable decay times of certain wavelengths, it may be advantageous to select specific wavelengths based on their respective decay times. For example, wavelengths that have decay times that would allow sufficient time for a user to scan and/or image the radiation emitted by the photoluminescent label are preferable to those that decay quickly and would not provide a user sufficient time to scan and/or image the photoluminescent label.

Figure 5:
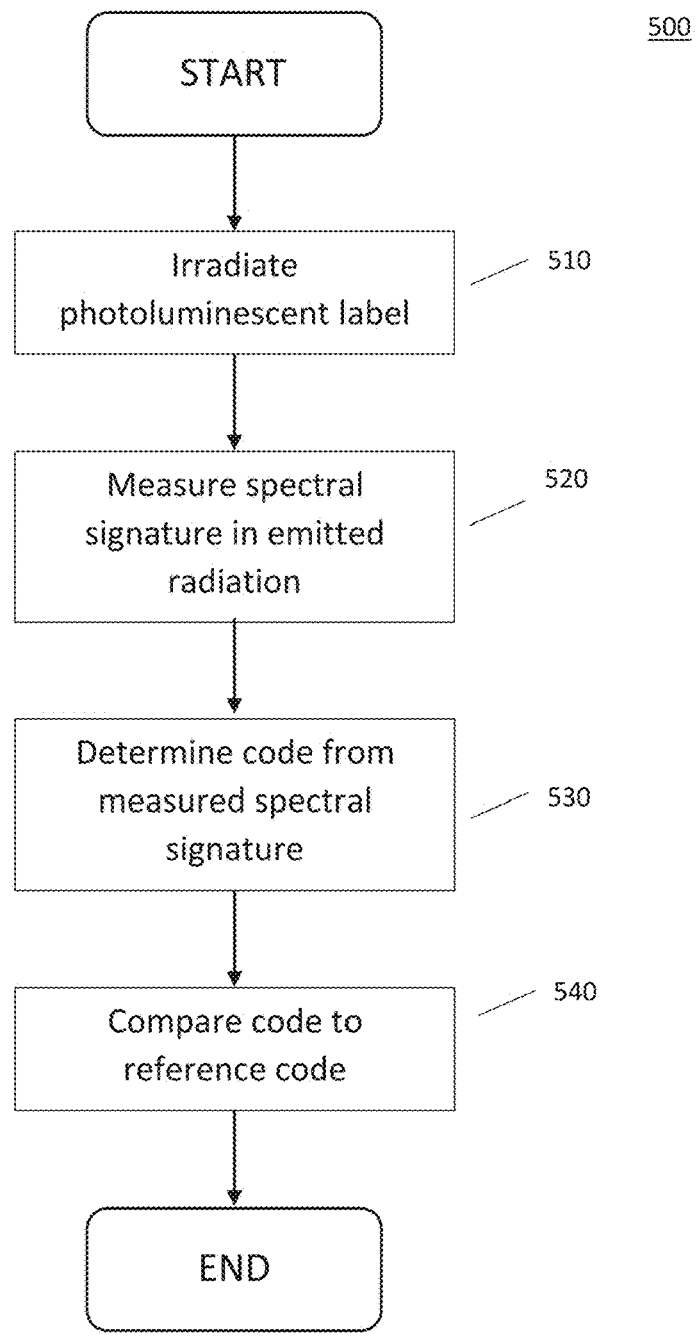
FIG. 5 is a flow diagram of an exemplary method according to certain exemplary embodiments of the present invention.

FIG. 5 shows an exemplary flow diagram 500 illustrating an exemplary operation of a photoluminescent system, such as system 300 shown in FIG. 3, for authenticating an item. As described in step 510, a radiation/excitation source 302 may irradiate photoluminescent label 306. After the photoluminescent label 306 has absorbed the radiation, the photoluminescent material emits emitted radiation. Accordingly, as shown in step 520, sensor 304 is used to measure the spectral signature in the emitted radiation. As described herein, the spectral signature, which may include a patterned spectrum or a spatial pattern or certain spectral intensities, defines the code encoded in photoluminescent label 306. In step 530, the code is determined from the measured spectral signature. In step 540, the code, which was determined from the measured spectral signature, is compared against reference codes stored in a database. This comparison provides authentication of the item to which photoluminescent label 306 is attached depending on whether or not the deciphered code and the stored reference codes match. Optionally, the process can be repeated to authenticate a subsequent item if the item is found not to be authentic.

Figure 6:
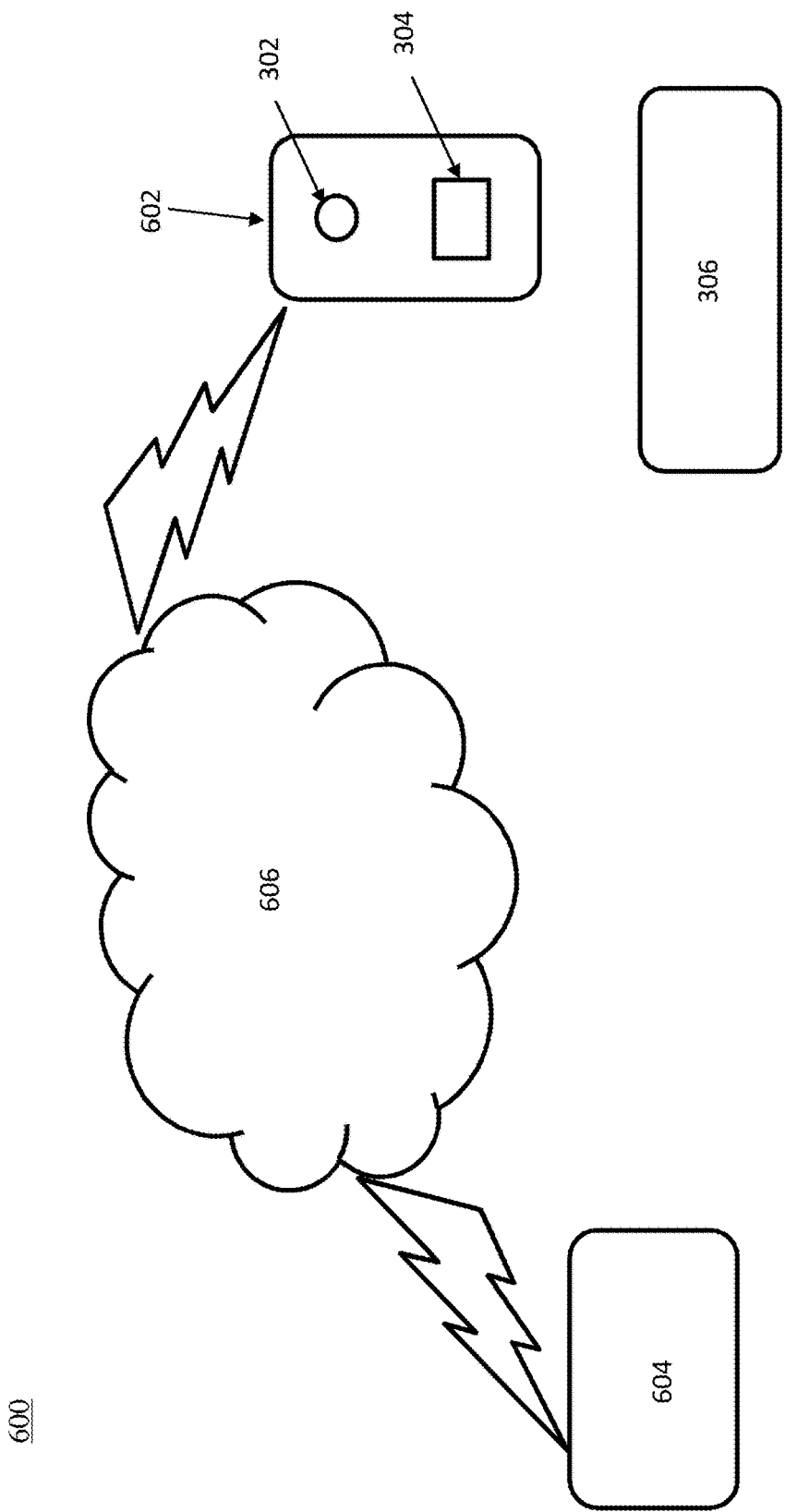
FIG. 6 is a diagram of an exemplary photoluminescent authentication system according to certain exemplary embodiments of the present invention.

FIG. 6 shows an exemplary system 600 that may be employed to authenticate an item using the photoluminescent labels described herein. For example, system 600 includes a computing device 602, which may include radiation/excitation source 302 and sensor 304. Computing device 602 may be any computing device that could incorporate a radiation/excitation source 302 and sensor 304, such as a smartphone, a tablet, or a personal data assistant (PDA). Alternatively, radiation/excitation source 302 and sensor 304 may be standalone devices that operate independent of a computing device. As described herein, the radiation/excitation source 302 may irradiate an exemplary photoluminescent label, and sensor 304 may measure the radiation emitted by the photoluminescent label, including the spectral signature. The computing device 602 may then determine the code from the measured spectral signature of the radiation emitted by the photoluminescent label. Alternatively, this processing may be performed by a remote computing device. Subsequently, the code or the measured spectral signature may be compared to a database of reference codes or spectral signatures. The database of reference codes may be stored locally on the scanning, imaging, or sensing device or remotely on a separate computing device. As shown in FIG. 6, to complete the authentication, the computing device 602 may compare the code or the measured spectral intensities to the reference codes or spectral signature stored in a database 604. Although FIG. 6 illustrates this comparison being performed via a network 606 to a remote database 604, other embodiments contemplate database 604 being local to computing device 602.

Further, in some embodiments, the item being authenticated may include an identifying label, such as, e.g., a barcode, a QR code, or a magnetic code, to enable correlation of the code or the measured spectral intensities to the item being authenticated. In a particular embodiment where computing device 602 is a smartphone or tablet, the transmission via the network 606 may be done over a cellular data connection or a Wi-Fi connection. Alternatively, this can be performed with a wired connection or any other data transport mechanisms.

Figure 7:
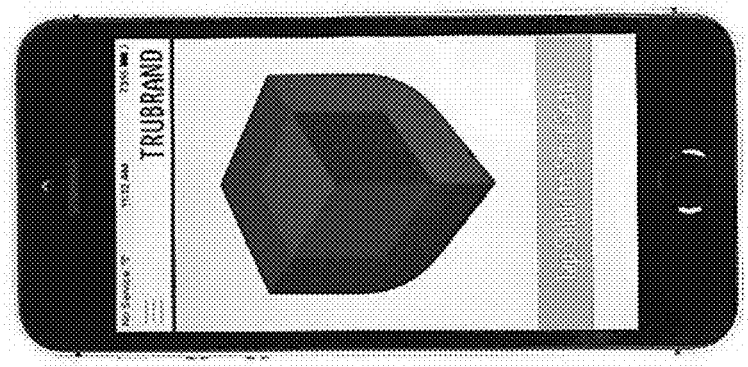
FIG. 7 is an illustration of an exemplary screenshot of an exemplary photoluminescent authentication application according to certain exemplary embodiments of the present invention.

In certain embodiments of the present invention where a computing device, such as a smartphone or tablet, is utilized for authenticating an item, a software application may be used to simplify the authentication process. FIG. 7 shows an exemplary screen shot of a software application that may be utilized on a smartphone for authenticating an item. The exemplary application may be configured to be executed on any mobile platform, such as Apple's iOS or Google's Android mobile operating system. When the application is run, the software application may provide instructions to a user on properly irradiating/exciting and scanning or imaging the photoluminescent label. Once irradiating and scanning of the photoluminescent label is complete, the application may facilitate comparison of the measured spectral signature and/or the measured code with a reference database storing certain reference codes or spectral signatures to authenticate the item. Further, the application may provide a message or other indicator informing the user of the result of the authentication. For example, the application may provide a text, graphical, or other visual indicator on the screen of the smartphone showing the results of the authentication. Alternatively, the application may provide audible and/or tactile indicators conveying the results of the authentication.

One exemplary embodiment of the present invention includes verifying the authenticity of banknotes, e.g., currency, using a remote device such as a smartphone. Implementing the detection techniques described herein, an application on the smartphone may be used both to verify the authenticity of banknotes and determine the denomination (i.e., monetary value) of the banknotes. Thus, according to the present invention, a smartphone may be used to both authenticate and denominate banknotes using a physical signature placed on or embedded in the banknotes.

The smartphone application for authenticating and denominating banknotes may include several useful features. The application may be used and is highly reliable in any lighting environment, including total darkness. No imaging of the banknotes by the application is required. The application may be implemented and operated by the user's touch through the smartphone's touch-sensitive screen. Alternatively, the application may be configured for visually impaired users or for voice controlled functionality and audible reporting. In particular, the application may be operated by a user based on voice controlled instructions recognized by the smartphone application and obtained through the smartphone's microphone. The result or determination by the smartphone of the authentication and denomination of banknotes may be reported or stated audibly to the user through the application by operation of the smartphone's speaker.

In embodiments such as using a smartphone application for authenticating and denominating banknotes, the application may be customizable for particular solutions. For example, the application may be customized with a queueing feature to contact or communicate with a central bank's website using remote communication services, such as cellular service or wireless services over the Internet. Such contact or communications between the user's smartphone and the central bank may be conducted in real time to provide accurate authentication and reporting and financial information.

Further, the smartphone application for authenticating and denominating banknotes may obtain location information using the smartphone's global positioning system (GPS) functionality to send a notification or report to a remote central authority or central bank of the user's location in the event the application determines a banknote to be fraudulent or suspect. In this manner, the smartphone application can provide the GPS location of the source of a fraudulent or suspect banknote with a central authority or central bank using remote communication services, such as cellular service or wireless services over the Internet, to provide real-time information regarding the authentication and denomination functions so that the central authority may conduct an immediate investigation into the source of the fraudulent or suspect banknote.

According to certain exemplary embodiments of the present invention, the exemplary photoluminescent label may also have a tamper resistant feature. For example, the photoluminescent label may be configured such that after the photoluminescent material is adhered to a surface, an individual may be prevented from detaching the photoluminescent material and/or the photoluminescent label in a manner that maintains the integrity of the photoluminescent material and/or the photoluminescent label. For example, any of photoluminescent labels 100, 110, 200, or 210 may be configured such that the label may not be removed intact such that if an individual were to tamper with the label, it would render the photoluminescent label inoperable or create a clear visual indication that the photoluminescent label had been tampered with.

The embodiments and examples above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of this disclosure. For a better understanding of the invention, its operating advantages and the specific objects attained by its uses, reference should be had to the accompanying drawings and descriptive matter in which there are illustrated exemplary embodiments of the invention.

What is claimed is:

1. A system for authenticating an item, the system comprising:
   a label having a surface and comprising a photoluminescent material capable of absorbing an incident radiation from a radiation source and emitting an emitted radiation having a spectral signature with a decay time after removal of the radiation source; and
   a photoauthentication device comprising:
      the radiation source configured to provide the incident radiation directly proximate to the photoluminescent material; and
      a camera configured to measure the emitted radiation directly proximate from the photoluminescent material at predefined time intervals during the decay time;
   wherein the spectral signature includes spectral intensities for a first wavelength and a second wavelength at a first time in the decay time and spectral intensities for the first wavelength and the second wavelength at a second time in the decay time, wherein the photoauthentication device is configured to communicate with an application to verify the authenticity of the item, wherein the application is configured to report a result of verifying the authenticity of the item, and wherein the photoauthentication device is configured to provide the incident radiation and measure the emitted radiation during a single motion of the photoauthentication device across the surface of the label.

2. The system of claim 1, wherein the spectral signature defines a measured code.

3. The system of claim 2, wherein at least one of the first and second wavelengths in the emitted radiation is within a spectrum of visible light.

4. The system of claim 1, wherein the spectral signature includes a spectral pattern or a spatial pattern.

5. The system of claim 1, wherein the spectral signature includes spectral intensities for a third wavelength at the first time and the second time.

6. The system of claim 1, wherein the photoauthentication device is a smartphone or a tablet.

7. A system for authentication, the system comprising:
a substrate having a surface and comprising a photoluminescent material having a decay time, the photoluminescent material being configured to absorb an incident radiation from a radiation source and to emit an emitted radiation having a spectral signature after removal of the radiation source; and
a photoauthentication device comprising:
the radiation source configured to provide the incident radiation directly proximate to the photoluminescent material; and
a camera configured to measure the emitted radiation directly proximate from the photoluminescent material at predefined time intervals during the decay time after removal of the radiation source,
wherein the spectral signature includes spectral intensities for a first wavelength and a second wavelength at a first time in the decay time and spectral intensities for the first wavelength and the second wavelength at a second time in the decay time, and
wherein the photoauthentication device is configured to provide the incident radiation and measure the emitted radiation during a single motion of the photoauthentication device across the surface of the substrate.

8. The system of claim 7, wherein the spectral signature defines a measured code.

9. The system of claim 8, wherein the measured code is compared to a predetermined code to determine authentication.

10. The system of claim 7, wherein the spectral signature includes a spectral pattern or a spatial pattern.

11. The system of claim 7, wherein the spectral signature includes spectral intensities for a third wavelength at the first time and the second time.

12. The system of claim 7, wherein the photoauthentication device is a smartphone or a tablet.

13. The system of claim 7, wherein at least one of the first and second wavelengths in the emitted radiation is within a spectrum of visible light.

14. The system of claim 7, wherein the substrate is configured to be incorporated into a currency.

15. A method for authenticating an item, comprising:
irradiating, with a radiation source, a substrate having a surface and comprising a photoluminescent material having a decay time and configured to absorb an incident radiation and to emit an emitted radiation having a spectral signature after removal of the radiation source;
measuring, with a camera, the emitted radiation from the photoluminescent material at predefined time intervals during the decay time after removal of the radiation source;
generating, with a computing device, a code based on the spectral signature; and
comparing, with the computing device, the code to a predetermined reference code,
wherein a photoauthentication device comprises the radiation source, the camera, and the computing device,
wherein the spectral signature includes spectral intensities for a first wavelength and a second wavelength at a first time in the decay time and spectral intensities for the first wavelength and the second wavelength at a second time in the decay time,
wherein the radiation source is configured to provide the incident radiation directly proximate to the photoluminescent material,
wherein the camera is configured to measure the emitted radiation directly proximate from the photoluminescent material, and
wherein the photoauthentication device is configured to provide the incident radiation and measure the emitted radiation during a single motion of the photoauthentication device across the surface of the substrate.

16. The method of claim 15, wherein the spectral signature defines a code.

17. The method of claim 15, wherein the photoauthentication device is a smartphone or a tablet.

* * * * *